United States Patent
Chen et al.

(10) Patent No.: US 6,752,953 B2
(45) Date of Patent: Jun. 22, 2004

(54) METHOD FOR MANUFACTURING HARD NON-GELATIN PHARMACEUTICAL CAPSULES

(75) Inventors: Gan-Lin Chen, Taipei (TW); Chien-Yuan Lee, Hsinchu (TW); Cheng-Hsiung Liu, Taichung (TW)

(73) Assignee: Yung Shin Pharmaceutical Co., Ltd., Taichung (TW)

(*) Notice: Subject to any disclaimer, the term of this patent is extended or adjusted under 35 U.S.C. 154(b) by 379 days.

(21) Appl. No.: 09/998,317

(22) Filed: Dec. 3, 2001

(65) Prior Publication Data

US 2003/0104047 A1 Jun. 5, 2003

(51) Int. Cl.$^7$ ................................................. C08J 5/00
(52) U.S. Cl. ................................. 264/330; 264/331.21
(58) Field of Search ............................ 264/330, 331.21

(56) References Cited

U.S. PATENT DOCUMENTS

| | | | |
|---|---|---|---|
| 3,617,588 A | * 11/1971 | Langman | .................... 264/486 |
| 4,001,211 A | 1/1977 | Sarka | |
| 4,138,013 A | 2/1979 | Okajima | |
| 4,780,316 A | 10/1988 | Brox | |
| 4,917,885 A | * 4/1990 | Chiba et al. | ................. 206/530 |
| 4,993,137 A | * 2/1991 | Muto et al. | .................... 29/451 |
| 5,571,651 A | 11/1996 | Inaba et al. | |
| 5,614,217 A | 3/1997 | Chprich et al. | |
| 5,641,512 A | 6/1997 | Cimiluca | |
| 5,698,155 A | 12/1997 | Grosswald et al. | |
| 5,756,123 A | 5/1998 | Yamamoto et al. | |
| 5,882,680 A | 3/1999 | Suzuki et al. | |
| 5,965,150 A | 10/1999 | Wada et al. | |
| 5,985,321 A | 11/1999 | Brox et al. | |
| 6,214,376 B1 | 4/2001 | Gennadios | |
| 6,214,378 B1 | 4/2001 | Tanida et al. | |
| 6,238,696 B1 | 5/2001 | Wang | |
| 6,248,354 B1 | 6/2001 | Firestone et al. | |
| 6,280,767 B1 | 8/2001 | Sano et al. | |

* cited by examiner

Primary Examiner—Stephen J. Lechert, Jr.
(74) Attorney, Agent, or Firm—Fei-Fei Chao; Venable LLP

(57) ABSTRACT

The present invention provides a method for manufacturing a non-gelatin hard capsule shell. The hard capsule shell is made by a heat-melting method which involves heating a capsule forming composition (preferably in powdery form) in a mold, followed by inserting a pestle into the mold to coat the melted capsule forming composition onto the pestle. The hard capsule shell thus formed, after hardened and dried, is removed from the pestle. This method has the advantages over the conventional "dip molding method" for not requiring the capsule forming composition to be pre-dissolved in solution so that no solvent is used in preparing the capsule forming composition. Also, by inserting a pestle into a mold, a pressure is imposed so as to ensure uniform coating of the capsule forming composition to the pestle. The present invention also provides a capsule forming composition which comprises a polymer and optionally a plasticizer and an apparatus for making the non-gelatin hard capsule shell.

11 Claims, No Drawings

METHOD FOR MANUFACTURING HARD NON-GELATIN PHARMACEUTICAL CAPSULES

FIELD OF THE INVENTION

The present invention relates to a method for manufacturing a non-gelatin hard capsule shell. The hard capsule shell is made by a heat-melting method which involves heating a capsule forming composition (preferably in powdery form) in a mold, followed by inserting a pestle into the mold to coat the melted capsule forming composition onto the pestle. The hard capsule shell is formed after hardened and dried, and removed from the pestle. The present invention also relates to a capsule forming composition which comprises a polymer and optionally a plasticizer. The polymer is preferred to be a cellulose or cellulose derivative, a polymer or copolymer of acrylate or acrylate derivative, a vinyl polymer, a polyolefin, poly(2-ethyl-2-oxazoline), or aginate. Finally, the present invention relates to an apparatus for making the hard capsule shell.

BACKGROUND OF THE INVENTION

Pharmaceutical capsules with telescopically engaged body and cap portions are called hard capsules or hard shell capsules. The most frequently used pharmaceutical capsules are generally made of gelatin. Optionally, plasticizer such as glycerin and sorbitol, opaque agent, dye, pigment and other additives can be blended in.

Gelatin is manufactured by the hydrolysis of animal by-products which contain collagen, which is usually found in animal bones, animal skins, and white animal connective tissues. The collagen-containing material is boiled in water, leaving behind the colorless or pale yellow protein which constitutes the hydrophilic colloid material of the gelatin.

The techniques for manufacturing the gelatin capsules are well developed. In general, a capsule molding pin is immersed in a gelatin aqueous solution and then withdrawn therefrom. The gelatin solution adhering to the pin is dried, thus obtaining the capsule shell. Some of the representative hard gelatin capsules include Warner-Lambert Company's PRE-FIT™, SNAP-FIT™, and CONI-SNAP™ series of hard gelatin capsules and Scherer's LOX-IT™ hard gelatin capsules.

However, because the primary sources of gelatin are from animals (such as bovine, pigs etc), gelatin-made capsules are not widely accepted by consumers. For example, Vegetarians, the Hebrews, and the Muslims do not ingest pigs and by-products of pigs. Also, Vegetarians and the Hindus will not eat beef or by-products of beef. These people are generally unwilling or feeling uneasy to utilize gelatin capsules for their medications or dietary supplements. Recently, there has been concerned about cross-species contamination. For example, the outbreak of bone spongiform encephalopathy, also known as BSE or "Mad Cow Disease," suggests that a disease initially infested in cows can be transmitted to humans. Thus, the use of gelatin capsules becomes a concern and it is more desirable to replace gelatin capsule with capsules derived from other natural or synthetic sources.

Medical capsules using a base other than gelatin are also known in the art. Typically, capsules based on water-soluble cellulose derivatives are widely used. For example, in 1950, U.S. Pat. No. 2,526,683 to Murphy first described a process for preparing methyl cellulose medicinal capsules by a so-called "dip coating" or "dip molding" process. The process consists of dipping a capsule forming pin pre-heated to 40–85° C. into a cellulose ether solution kept at a temperature below the incipient gelation temperature (10–30° C.), withdrawing the pins at a predetermined withdrawal speed and then placing the pins in ovens kept at temperatures above the gelation temperature (45–85° C.), exposing the pins to a lower temperature first and then gradually to higher temperature until the film is dry. The dry capsule is then stripped, cut to size, and the body and caps are fitted together. The Murphy patent is the original patent for the manufacture of methyl cellulose capsule. Its drying process uses infrared lamps and cooling by air.

The methyl cellulose capsules according to Murphy's U.S. Pat. No. 2,526,683 have several advantages over conventional gelatin capsules, such as resistance to microorganisms and greater stability under extreme humidity conditions. However, these capsules failed to dissolve in the gastrointestinal fluid at body temperature in an acceptable time.

Sarkar's U.S. Pat. No. 4,001,211 descibe a medicinal capsule using thermal gelling cellulose ethers such as methyl cellulose and hydroxypropylmethyl cellulose. These cellulose ethers are soluble in cold water and insoluble in hot water. The viscosity of aqueous solutions decreases with the rise in temperature and then rapidly increases through a relatively narrow range of temperature with gel formation a few degrees above the temperature at which minimum viscosity is observed. Sarkar's capsules are prepared by a pin dip coating process by blending a water soluble methyl and $C_2$–$C_3$ hydroxyalkyl cellulose ethers to achieve an essentially Newtonian dip coating solution. Blends of low viscosity methyl cellulose and hydroxypropylmethyl cellulose provide particularly suitable dip solution properties, gel yield strength, and capsule dissolution rates.

Muto's U.S. Pat. No. 4,993,137 is directed to the manufacture of capsules made from the improved methyl cellulose ether of Sarkar. Muto discloses a process for gelling the solution by dipping solution coated pins into thermally controlled water.

Grosswald et al.'s U.S. Pat. No. 5,698,155 describe a method and apparatus to manufacture pharmaceutical capsules which use an aqueous solution of a thermogelling cellulose ether composition and use capsule body pins and capsule cap pins as molds. The method involves heating the pins, dipping the pins into the cellulose-containing aqueous solution to cause the solution to gelatinize on the surface of the pins, removing the pins, and drying the gelatinized solution on the surface of the pins to form the capsule bodies and capsule caps.

Yamamoto et al.'s U.S. Pat. No. 5,756,123 discloses a capsule shell containing 79.6–98.7% by weight of a hydroxypropylmethyl cellulose (HPMC) as a water-soluble cellulose derivative base, 0.03–0.5% by weight of carrageenan as a gelling agent, and 0.14–3.19% by weight of a potassium ion and/or a calcium as a co-gelling agent. The capsule shell is prepared by blending the HPMC with carrageenan in the water to form an aqueous solution, and drying the aqueous solution to form a capsule shell using the conventional immersion molding method.

In the invention to be presented in the following sections, a novel heat-melting method for preparing hard capsule shell is provided. The method involves adding a capsule forming composition to a mold. The composition contains a polymer and optionally a plasticizer but does not contain any solvent. The polymer is not a gelatin. The capsule forming composition is heated inside the mold to become a melted solution.

A pestle which can fittedly insert into the mold and which is also heated to above the melting temperature of the composition is then inserted into the mold with pressure to allow the melted composition evenly coated onto the pestle. The pestle with melted composition is then withdrawn from the mold and upon drying, the capsule is removed from the pestle. This method differs from the conventional dip coating method for no gelling solution or solvent is involved. The capsule shell formed by this method is cost-effective and does not have the common imperfections found in capsules made by conventional dip coating method, such as wrinkles, starred ends and corrugations.

SUMMARY OF THE INVENTION

The present invention provides a method for manufacturing a hard capsule shell. The method comprises: (1) adding a capsule forming composition to a mold having at least an opening shaped as a capsule cap or a capsule body; (2) heating the mold and a capsule forming pestle having a diameter smaller than the mold opening to a temperature which is above a melting temperature of the capsule forming composition; (3) applying pressure to insert the heated capsule forming pestle into the opening of the heated mold so that the pestle is in contact with the capsule forming composition; (4) withdrawing the heated pestle from the heated mold so that the melted capsule forming composition is evenly coated onto the heated pestle; (5) cooling and drying the capsule forming composition on the pestle; and (6) removing the dried capsule forming composition from the pestle. The capsule forming composition contains a non-gelatin polymer and optionally a plasticizer. Preferably, The capsule forming composition does not contain any solvent. A solvent in the present invention is defined as any liquid that is capable of dissolving the capsule forming composition. Examples of solvent in this context include water, any buffer solutions, or any organic solvents which are commonly and conventionally used to prepare a dip capsule forming solution. Because the present invention uses a heat-melting method, the capsule forming composition in the powdery form can be added to the mold and becomes melted solution without the assistance of any solvent.

Preferably, the mold and the capsule forming pestle are made of stainless steel, although any kind of material that can sustain a melting temperature of the capsule forming composition can be used. The melting temperature of the capsule forming composition depends on the kind of polymer that is used in making the capsule.

The polymer that can be used in making the present hard capsule shell can be divided into the following groups of materials: (1) cellulose- or cellulose derivative-based material, which include, but are not limited to, cellulose, cellulose ester, cellulose ether, cellulose nitrate, cellulose triacetate, cellulose acetate phthate, methyl cellulose, ethyl cellulose, hydroxypropyl cellulose, hydroxypropyl methylcellulose, and hydroxypropyl methylcellulose phthalate. (2) polymer or copolymer of acrylate or acrylate derivative, which include, but are not limited to, polyacrylate, polymethylacrylate, poly(acrylate-methylacrylate), poly(methacrylate-methylmethacrylate), poly(ethylacrylate-methylmethacrylate), poly(ethylacrylate-methylmethacrylate-trimethylammonioethylmethacrylate chloride), and poly(ethylacrylate-methylmethacrylate-trimethylammonioethylmethacrylate chloride); (3) polyolefin which include, but are not limited to, polyethylene, polypropylene, and polybutylene; (4) vinyl polymer which include, but are not limited to, polyvinyl chloride, polyvinyl acetate, polyvinyl alcohol, polystyrene and polyacrylonitrile. Additionally, polymer such as poly (2-ethyl-2-oxazoline) or aginate can also be used for making the capsule.

The plasticizer that can be used in forming the capsule forming composition include, but are not limited to, glycerine, propylene glycol, polyethylene glycol (PEG 200–6000), diethyl phthalate, dibutyl phthalte, dibutyl sebacate, triethyl citrate, acetyltriethyl citrate, acetyltributyl citrate, tributyl citrate, triacetyl glycerine, castor oil, acetylated monoglyceride, and coconut oil (purified form is preferred).

The present invention also provides a hard capsule shell. The hard capsule shell contains a capsule forming composition which comprises a polymer and a plasticizer, the polymer is not gelatin, and the capsule forming composition does not contain a solvent. It is preferred that the plasticizer constitutes about 0%–40%, and most favorably about 0.01–20%, by weight of the capsule forming composition.

Also preferably that the hard capsule shell is prepared by adding the capsule forming composition to a mold having at least an opening shaped as a capsule cap or a capsule body; heating the mold and a capsule forming pestle having a diameter smaller than the mold opening to a temperature above the melting temperature of the capsule forming composition; applying pressure to insert the heated capsule forming pestle into the opening of the heated mold to allow the melted capsule forming composition to be evenly coated onto the pestle; withdrawing the heated pestle from the heated mold so that the coated capsule forming composition can be further cooled and dried and removed from the pestle to form the capsule shell.

Finally, the present invention provides an apparatus for making a hard capsule shell. The apparatus contains two major parts, which are: (1) a mold, which contains at least an opening shaped as a capsule cap or a capsule body; and (2) a capsule forming pestle which is also shaped as a capsule cap or a capsule body but its diameter is smaller than the mold opening (the diameter of the pestle should be similar to the inner diameter of the capsule shell). The apparatus is operated by first adding the capsule forming composition to the mold; then, the mold with the capsule forming composition and the pestle are heated to above a melting temperature of said capsule forming composition (to convert the powdery composition to a melted solution), followed by inserting the pestle into the mold with pressure, and withdrawn the pestle from the mold so that the capsule forming composition is evenly coated onto the pestle. The capsule forming composition can be further cooled, dried and removed from the pestle to form the hard capsule shell.

Both the mold and the capsule forming pestle are preferably made of stainless steel. It is possible to further include a a kiln in the apparatus for hardening and drying the capsule forming composition. The kiln is preferred to be kept at a temperature which is above the incipient gelation temperature of the capsule forming composition. It is also preferred that the capsule forming composition is dried while it is coated onto the pestle.

Optionally, the pestle is attached to a device which facilitates the insertion and/or withdrawal of the pestle to and from the mold.

DETAILED DESCRIPTION OF THE INVENTION

The term "capsules" used in this invention is referred to as hard shell capsules (optionally containing medicament) each having telescopically engaged body and cap portions.

The method of making non-gelatin capsules, such as cellulose capsules, is well developed. The conventional method for making the cellulose capsules is the so-called "dip coating method," which involves dipping a pin shapes as a capsule cap or capsule body in an aqueous solution containing the capsule composition.

The method created by the present invention does not use a "dip coating method," rather, it uses a so-called "heat-melting method" to melt the capsule forming composition in a mold, preferably made of stainless steel so that it can sustain high melting temperature. The capsule shell is formed after a pre-heated pestle (also preferably made of stainless steel) which can fittedly inserted into the mold is inserted. The pressure applied by the pestle ensures that the melted capsule forming composition is evenly coated onto the pestle. The pestle is then retrieved from the mold, taking the coated capsule forming composition with it. The capsule forming composition is then dried and removed from the pestle to become the capsule shell.

The "heat-melting method" has the advantages of not requiring the preparation of an aqueous solution containing the capsule forming composition and is therefore superior to the conventional method. In particular, it is time-saving and cost-effective because it does not involve the dipping of pins in the solution, removing the pins from the solution at set speed, and gelling the capsules at successively warmer temperature, as suggested by Murphy's U.S. Pat. No. 2,526,683.

The capsule forming composition used in the present invention comprises a polymer and optionally a plasticizer. Also optionally, colorants, pigments and other additives can be added.

There are four (4) major classes of polymers that are suitable for use in a capsule forming composition of the present invention, which are: (1) cellulose or cellulose derivatives; (2) polymers or copolymers of acrylate or acrylate derivative; (3) vinyl polymers; and (4) polyolefins. In addition, poly(2-ethyl-2-oxazoline) or aginate has also been tested to be useful for making the capsules of the present invention.

Cellulose or cellulose derivatives that are suitable for use in preparing capsules include natural or synthetic substances, such as cellulose, cellulose ester, cellulose ether, cellulose nitrate, cellulose triacetate, cellulose acetate phthate (CAP), methyl cellulose, ethyl cellulose, hydroxypropyl cellulose (HPC), hydroxypropyl methylcellulose (HPMC), and hydroxypropyl methylcellulose phthalate (HPMCP).

The preferred cellulose polymers include hydroxypropyl cellulose (HPC), hydroxypropyl methylcellulose (HPMC), cellulose acetate phthalate (CAP), and hydroxypropylmethylcellulose phthalate (HPMCP).

Hydroxypropyl methylcellulose (National Formulary XIII) and cellulose acetate phthalate (U.S.P. XVIII) are sometimes referred to as HPMC and CAP, respectively. Hydroxypropyl methylcellulose phthalate is sometimes referred to as HPMCP. At the present time, at least two grades or types of HPMCP are commercially available from the Shinetsu Chemical Company of Tokyo, Japan. These grades or types are known as HP-50 and HP-55. HP-50 has 20–25% methoxyl content, 8–12% hydroxypropoxyl content, and 20–27% carboxybenzoyl content. HP-55 has 18–22% methoxyl content, 6–10% hydroxylpropoxyl content, and 27–35% carboxybenzoyl content. Both HP-50 and HP-55 are soluble in water by the addition of base. HP-50 is dissolved above pH 5. HP-55 is dissolved above pH 5.5.

The preferred polymers or copolymers of acrylate or acrylate derivative include, but are not limited to, polyacrylate, polymethylacrylate, poly(acrylate-methylacrylate), poly(methacrylate-methylmethacrylate), poly(ethylacrylate-methylmethacrylate), poly(ethylacrylate-methylmethacrylate-trimethylammonioethylmethacrylate chloride), and poly(ethylacrylate-methylmethacrylate-trimethylammonioethylmethacrylate chloride).

For example, the copolymer of methacrylic acid and methacrylic acid alky ester has the following structural unit:

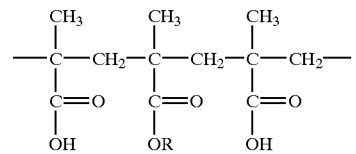

wherein R is a lower alkyl group, in particular, a methyl or ethyl group.

Methacrylic acid/ester copolymer can be prepared according to a number of methods. There are many grades or types of methacrylic acid/ester copolymers that are commercially available. For example, Rohm & Haas Company of Tokyo, Japan, has the so-called Eudragit® series containing various polymethacrylic acid-methacrylic acid copolymer such as Eudragit®-E, L, S, RL, RS, NE. Most of these copolymer are soluble in water when base is added. The preferred Eurdragit® polymer series to be used in the present invention include Eurdragit®-RS100 and RL-100.

Eudragit L100 contains poly(methacrylic acid, methylmethacrylate) at 1:1 ratio and is sold as solid powder. Eudragit®-S100 contains poly(methacrylic acid, methylmethacrylate) at a 1:2 ratio and is sold as solid powder. Eudragit®-L100-55 contains poly(methacrylic acid, ethylacrylic) at a 1:1 ratio and is sold as solid powder. Eudragit®-E100 contains polyaminomethacrylate-(poly [butylmethacrylate, (2-dimethylaminoethyl)-methacrylate, methylmethacrylate]) at a 2:1 ratio and is sold as solid polymer granules. Eudragit®-RL100 contains poly (ethylacrylate, methylmethacrylate, trimethylammonioethylmethacrylate chloride) at a 1:2:0.2 ratio and is sold as solid polymer granules. Eudragit®-RS100 contains poly (ethylacrylate, methylmethacrylate, trimethylammonioethylmethacrylate chloride) at a 1:2:0.1 ratio is sold as solid polymer granules.

Methacrylic acid/ester copolymers are anionic copolymers, and are generally used as intestinal or enteric delivery due to its properties of being soluble only at pH 5.5 or higher. For example, anionic copolymer Eudragit®-S is soluble at pH 7.0. Eudragit S or L is also soluble at pH 7.0 or higher. As for Eudragit®-RS, it is hardly soluble in water.

The preferred vinyl polymers include, but are not limited to, polyvinyl chloride, polyvinyl acetate, polyvinyl alcohol, polystyrene and polyacrylonitrile.

Examples of polyolefins include, but are not limited to, polyethylene, polypropylene, and polybutylene.

Optionally, plasticizers can be added to the polymer to form the capsule forming compositions of the capsules. Examples of the plasticizers that are suitable to be used with the polymer include (1) polyglycols such as polypropylene glycol, polybutylene glycol and polyethylene glycol (PEG) (200–6000); (2) organic esters such as diethylphthalate (DEP), dibutylphthalate (DBP), dibutyl sebacate (DBS); (3) citrates such as triethyl citrate (TEC), acetyltriethylcitrate (ATEC), acetyltributylcitrate (ATBC), tributylcitrate (TBC), and triacetyl glycerine (triacetin); and (4) oils/glyerides such as castor oil, acetylated monoglyceride, and purified coconut oil.

The preferred plasticizers are polyethylene glycol (e.g., PEG 1000 and 4000), triethyl citrate, tributyl citrate, and triacetin. The preferred amount of plasticizers in the capsule forming compositions is 0%–40% by weight, most favorably 0.01% to 20% by weight.

The following examples are illustrative, and should not be viewed as limiting the scope of the present invention. Reasonable variations, such as those occur to reasonable artisan, can be made herein without departing from the scope of the present invention.

EXAMPLE 1

A hard capsule shell was prepared by the following procedures:
(1) adding about 65 mg of hydroxypropyl cellulose (HPC) as polymer to an opening of a mold made of stainless steel; the opening of the mold was shaped as either the capsule cap or the capsule body and with various sizes according to the standard requirements in the pharmaceutical industry; the diameter of the opening was the same as the external diameter of the capsule shell;
(2) heating the mold and a capsule forming pestle (which was also made of stainless steel) to about 160° C. until the HPC was completely melted; the pestle was also shaped as a capsule cap or a capsule body except that the diameter of the pestle was about the internal diameter of the capsule shell;
(3) inserting the pestle into the mold while the HPC was in melting condition, preferably with pressure to ensure the melted HPC was evenly coated onto the pestle;
(4) withdrawing the pestle from the mold; preferably a pulling device was connected to the pestle to facilitate the pulling of the pestle out of the mold;
(5) harding and drying the HPC coated on the pestle; preferably a kiln was provided so that the pestle with coated HPC was dried in the kiln until the HPC was completely gelled;
(6) removing the HPC capsule from the pestle.

EXAMPLE 2

A hard capsule shell was prepared by the following procedures:
(1) mixing about 65 mg of hydroxypropyl cellulose (HPC) as polymer with about 7.2 mg of PEG 1000 as plasticizer to form a capsule forming composition (the plasticizer is about 10% by weight of the capsule forming composition); adding the capsule forming composition to an opening of a mold;
(2) heating the mold and a capsule forming pestle to about 120° C. until the HPC and PEG capsule forming composition was completely melted;
(3) inserting the pestle into the mold while the HPC and PEG capsule forming composition was in melting condition, preferably with pressure to ensure the melted capsule forming composition was evenly coated onto the pestle;
(4) withdrawing the pestle from the mold; preferably with a pulling device connected to the pestle to facilitate the pulling of the pestle out of the mold;
(5) harding and drying the capsule forming composition on the pestle; preferably a kiln was provided so that the pestle with coated capsule forming composition was dried in the kiln until the capsule forming composition was completely gelled;
(6) removing the gelled capsule forming capsule from the pestle.

The size and structure of the mold and the pestle was the same as those described in Example 1.

EXAMPLE 3

A hard capsule shell was prepared by the following procedures:
(1) dissolving 70 mg of Eudragit RS100 (as polymer) in acetone; mixing the dissolved Eudragit RS100 with 0.7 mg of triethyl citrate ("TEC") (as plasticizer) to form a capsule forming composition; evaporating the actone from the capsule forming composition at 50° C.; adding the capsule forming composition to an opening of a mold;
(2) heating the mold and a capsule forming pestle to about 120° C. until the Eudragit RS100 and TEC capsule forming composition was completely melted;
(3) inserting the pestle into the mold while the Eudragit RS100 and TEC capsule forming composition was in melting condition, preferably with pressure to ensure the melted capsule forming composition was evenly coated onto the pestle;
(4) withdrawing the pestle from the mold; preferably with a pulling device connected to the pestle to facilitate the pulling of the pestle out of the mold;
(5) harding and drying the capsule forming composition on the pestle; preferably a kiln was provided so that the pestle with coated capsule forming composition was dried in the kiln until the capsule forming composition was completely gelled;
(6) removing the gelled capsule forming capsule from the pestle.

The size and structure of the mold and the pestle was the same as those described in Example 1.

EXAMPLE 4

A hard capsule shell was prepared by the following procedures:
(1) dissolving 70 mg of Eudragit RL100 (as polymer) in acetone; mixing the Eudragit RL100 with 0.7 mg of tributyl citrate ("TBC") (as plasticizer) to form a capsule forming composition; mixing the dissolved Eudragit RS100 with 0.7 mg of triethyl citrate ("TBC") (as plasticizer) to form a capsule forming composition; evaporating the actone from the capsule forming composition at 50° C.; adding the capsule forming composition to an opening of a mold;
(2) heating the mold and a capsule forming pestle to about 180° C. until the Eudragit RL100 and TBC capsule forming composition was completely melted;
(3) inserting the pestle into the mold while the Eudragit RL100 and TBC capsule forming composition was in melting condition, preferably with pressure to ensure the melted capsule forming composition was evenly coated onto the pestle;
(4) withdrawing the pestle from the mold; preferably with a pulling device connected to the pestle to facilitate the pulling of the pestle out of the mold;
(5) harding and drying the capsule forming composition on the pestle; preferably a kiln was provided so that the pestle with coated capsule forming composition was dried in the kiln until the capsule forming composition was completely gelled;
(6) removing the gelled capsule forming capsule from the pestle.

The size and structure of the mold and the pestle was the same as those described in Example 1.

EXAMPLE 5

A hard capsule shell was prepared by the following procedures:

(1) adding about 70 mg of hydroxypropyl methylcellulose (HPMC) as polymer and about 7.8 mg of PEG 4000 (as plasticizer) to form a capsule forming composition (the plasticizer is about 10% by weight of the capsule forming composition); adding the capsule forming composition to an opening of a mold;

(2) heating the mold and a capsule forming pestle to about 200° C. until the HPMC and PEG capsule forming composition was completely melted;

(3) inserting the pestle into the mold while the HPMC and PEG capsule forming composition was in melting condition, preferably with pressure to ensure the melted capsule forming composition was evenly coated onto the pestle;

(4) withdrawing the pestle from the mold; preferably with a pulling device connected to the pestle to facilitate the pulling of the pestle out of the mold;

(5) harding and drying the capsule forming composition on the pestle; preferably a kiln was provided so that the pestle with coated capsule forming composition was dried in the kiln until the capsule forming composition was completely gelled;

(6) removing the gelled capsule forming capsule from the pestle.

The size and structure of the mold and the pestle was the same as those described in Example 1.

EXAMPLE 6

A hard capsule shell was prepared by the following procedures:

(1) adding about 70 mg of poly(2-ethyl-2-oxazoline) as polymer and about 7.8 mg of triacetin ("TA") (as plasticizer) to form a capsule forming composition (the plasticizer is about 10% by weight of the capsule forming composition); adding the capsule forming composition to an opening of a mold;

(2) heating the mold and a capsule forming pestle to about 120° C. until the poly(2-ethyl-2-oxazoline) and TA capsule forming composition was completely melted;

(3) inserting the pestle into the mold while the poly(2-ethyl-2-oxazoline) and TA capsule forming composition was in melting condition, preferably with pressure to ensure the melted capsule forming composition was evenly coated onto the pestle;

(4) withdrawing the pestle from the mold; preferably with a pulling device connected to the pestle to facilitate the pulling of the pestle out of the mold;

(5) harding and drying the capsule forming composition on the pestle; preferably a kiln was provided so that the pestle with coated capsule forming composition was dried in the kiln until the capsule forming composition was completely gelled;

(6) removing the gelled capsule forming capsule from the pestle.

The size and structure of the mold and the pestle was the same as those described in Example 1.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for manufacturing a hard capsule shell comprising:

adding a capsule forming composition to a mold having at least an opening shaped as a capsule cap or a capsule body; wherein said capsule forming composition comprises a polymer; wherein said polymer is not gelatin;

heating said mold and a capsule forming pestle having a diameter smaller than said mold opening to a temperature above a melting temperature of said capsule forming composition;

inserting said heated capsule forming pestle into said opening of said heated mold with pressure to contact said capsule forming composition;

withdrawing said heated pestle from said heated mold; wherein said capsule forming composition is melted and coated onto said heated pestle;

cooling and drying said capsule forming composition on said pestle; and removing said dried capsule forming composition from said pestle.

2. The method according to claim 1, wherein said mold and said capsule forming pestle are made of stainless steel.

3. The method according to claim 1, wherein said polymer is a cellulose or cellulose derivative.

4. The method according to claim 3, wherein said cellulose or its derivative is at least one selected from the group consisting of cellulose, cellulose ester, cellulose ether, cellulose nitrate, cellulose triacetate, cellulose acetate phthate, methyl cellulose, ethyl cellulose, hydroxypropyl cellulose, hydroxypropyl methylcellulose, and hydroxypropyl methylcellulose phthalate.

5. The method according to claim 1, wherein said polymer is polymer or copolymer of acrylate or acrylate derivative.

6. The method according to claim 5, wherein said polymer or copolymer of acrylate or acrylate derivative is at least one selected from the group consisting of polyacrylate, polymethylacrylate, poly(acrylate-methylacrylate), poly(methacrylate-methylmethacrylate), poly(ethylacrylate-methylmethacrylate), poly(ethylacrylate-methylmethacrylate-trimethylammonioethymethacrylate chloride), and poly(ethylacrylate-methylmethacrylate-trimethylammonioethylmethacrylate chloride).

7. The method according to claim 1, wherein said polymer is polyolefin which is one selected from the group consisting of polyethylene, polypropylene, and polybutylene.

8. The method according to claim 1, wherein said polymer is vinyl polymer which is at least one selected from the group consisting of polyvinyl chloride, polyvinyl acetate, polyvinyl alcohol, polystyrene and polyacrylonitrile.

9. The method according to claim 1, wherein said polymer is poly (2-ethyl-2-oxazoline) or aginate.

10. The method according to claim 1, wherein said polymer is mixed with a plasticizer.

11. The method according to claim 10, wherein said plasticizer is at least one selected from the group consisting of glycerine, propylene glycol, polyethylene glycol (PEG 200–6000), diethyl phthalate, dibutyl phthalte, dibutyl sebacate, triethyl citrate, acetyltriethyl citrate, acetyltributyl citrate, tributyl citrate, triacetyl glycerine, castor oil, acetylated monoglyceride, and coconut oil.

* * * * *

UNITED STATES PATENT AND TRADEMARK OFFICE
CERTIFICATE OF CORRECTION

PATENT NO. : 6,752,953 B2 Page 1 of 1
DATED : June 22, 2004
INVENTOR(S) : Gan-Lin Chen et al.

It is certified that error appears in the above-identified patent and that said Letters Patent is hereby corrected as shown below:

Title page,
Item [73], Assignee, after "Pharmaceutical" insert -- Industrial --.

Signed and Sealed this

Sixteenth Day of November, 2004

JON W. DUDAS
*Director of the United States Patent and Trademark Office*